(12) United States Patent
Anderson et al.

(10) Patent No.: US 10,646,639 B2
(45) Date of Patent: *May 12, 2020

(54) VALVED CONTAINER ASSEMBLY

(71) Applicant: Consort Medical PLC, Hempstead (GB)

(72) Inventors: Ian Anderson, Burwell (GB); Matt Ekman, Macclesfield (GB)

(73) Assignee: Consort Medical PLC, Hempstead (GB)

( * ) Notice: Subject to any disclaimer, the term of this patent is extended or adjusted under 35 U.S.C. 154(b) by 203 days.

This patent is subject to a terminal disclaimer.

(21) Appl. No.: 15/826,918

(22) Filed: Nov. 30, 2017

(65) Prior Publication Data

US 2018/0078701 A1 Mar. 22, 2018

Related U.S. Application Data

(63) Continuation of application No. 14/380,241, filed as application No. PCT/GB2013/050439 on Feb. 22, 2013, now Pat. No. 9,833,558.

(30) Foreign Application Priority Data

Feb. 22, 2012 (GB) .................................. 1203014.4

(51) Int. Cl.
*A61M 3/02* (2006.01)
*A61M 15/00* (2006.01)
(Continued)

(52) U.S. Cl.
CPC ........ *A61M 3/0279* (2013.01); *A61M 15/003* (2014.02); *A61M 15/0028* (2013.01);
(Continued)

(58) Field of Classification Search
CPC ........ A61M 3/0279; A61M 2005/3128; A61M 39/22; A61M 16/20; A61M 5/36;
(Continued)

(56) References Cited

U.S. PATENT DOCUMENTS 5,405,333 A 4/1995 Richmond
6,789,750 B1 9/2004 Heldt
(Continued)

FOREIGN PATENT DOCUMENTS

EP 0111796 A1 6/1984
FR 2750051 A1 12/1997
(Continued)

OTHER PUBLICATIONS

International Search Report and Written Opinion for PCT/GB2013/050439, dated Jun. 7, 2013.
(Continued)

*Primary Examiner* — Nilay J Shah
(74) *Attorney, Agent, or Firm* — Taft Stettinius & Hollister LLP; Stephen F. Rost

(57) ABSTRACT

A valved container assembly has a container for containing a fluid, extending in an axial direction, and having an open front end and a valve disposed in the container. A plunger element is disposed axially rearward of the valve and is axially moveable in the container. The plunger element is configured to increase the pressure of a fluid in a first volume of the container upon axial movement of the plunger element relative to the valve. The valve includes a channel bypassing a seal, the channel having a first opening in fluid communication with the atmosphere outside of the valved container assembly and a second opening selectively sealed from the first volume by a resilient seal. The resilient seal is moveable from a sealing configuration to an open configu-
(Continued)

ration upon the pressure of the fluid in the first volume exceeding a first pressure threshold.

19 Claims, 3 Drawing Sheets

(51) Int. Cl.
    *A61M 15/08*     (2006.01)
    *B05B 11/00*     (2006.01)
    *B05B 11/02*     (2006.01)
    *A61M 31/00*     (2006.01)
    *A61M 39/24*     (2006.01)
    *B05B 7/24*     (2006.01)
    *A61M 5/31*     (2006.01)
    *A61M 11/00*     (2006.01)

(52) U.S. Cl.
    CPC ............ *A61M 15/08* (2013.01); *A61M 31/00* (2013.01); *A61M 39/24* (2013.01); *B05B 7/24* (2013.01); *B05B 11/007* (2013.01); *B05B 11/02* (2013.01); *A61M 11/007* (2014.02); *A61M 15/0043* (2014.02); *A61M 2005/3128* (2013.01); *A61M 2039/242* (2013.01); *A61M 2202/0468* (2013.01); *A61M 2210/0618* (2013.01)

(58) Field of Classification Search
CPC .......... A61M 5/2459; A61M 2039/242; A61M 2039/2039; A61M 2039/2433; A61M 2039/244; A61M 2039/2466; A61M 11/007; A61M 2005/2451; A61M 5/16827; F16K 15/148
See application file for complete search history.

(56) References Cited

U.S. PATENT DOCUMENTS

2007/0225651 A1     9/2007   Rosenberg et al.
2009/0236374 A1*   9/2009   Pardes ................. A61F 9/0008
                                                       222/494

FOREIGN PATENT DOCUMENTS

| | | |
|---|---|---|
| FR | 2780051 A1 | 12/1999 |
| FR | 2793708 A1 | 11/2000 |
| GB | 2400040 A | 3/2005 |
| JP | 10057487 A | 3/1998 |

OTHER PUBLICATIONS

U.K. Search Report of Priority Application No. GB1203014.4, dated June 20, 2012.
Indian Office Action, Intellectual Property India, Indian Patent Application No. 7271/DELMP/2014, dated Jan. 22, 2019, 7 pages.

* cited by examiner

VALVED CONTAINER ASSEMBLY

This invention relates to a valved container assembly, and in particular to a valved container assembly having a self opening valve.

BACKGROUND

GB2400040 (Bespak plc) describes a closure member for a container, such as a vial, that seeks to facilitate the delivery of a metered dose of medicament, for example, in a nasal dispenser. In particular, GB2400040 describes a container or vial for a fluid, the container comprising a casing defining an interior for storage of the fluid and a closure member. The closure member comprises a body and at least one resilient projection to seal in a storage condition an outlet of the casing, wherein upon an increase in the pressure of the interior of the container the at least one resilient projection is deflected to accommodate outflow of fluid through the outlet. In one described embodiment, the closure member has a sealing portion that seals the closure member to the container about the circumference of the closure member, and pressure in the interior of the container is increased by displacing the closure member into the container. In another described embodiment, the container is part of a dispensing apparatus. In this embodiment, however, the sealing portion is separate to the closure member and forms a bung that is displaceable in the interior of the container to increase the pressure therein.

It is an object of the present invention to provide an alternative valved container assembly for dispensing a fluid.

BRIEF SUMMARY OF THE DISCLOSURE

The present invention is defined in the appended claims.

In accordance with a first aspect of the present invention there is provided a valved container assembly comprising:
- a container for containing a fluid, the container extending in an axial direction and having an open front end;
- a valve disposed in the container, the valved container assembly being configured so that forward axial movement of the valve relative to the container is inhibited; and
- a plunger element disposed axially rearward of the valve, the plunger element being axially moveable in the container and defining a first volume in the container between the plunger element and the valve, where the plunger element is configured to increase the pressure of the fluid in the first volume upon forward axial movement relative to the valve;

where the valve comprises:
- a permanent seal fluidly sealing the valve to the container about an entire perimeter of the valve; and
- a channel bypassing the permanent seal, the channel having a first opening in fluid communication with an atmosphere outside of the valved container assembly and a second opening selectively sealed from the first volume by a resilient seal;

wherein the resilient seal is moveable between a sealing configuration and an open configuration to selectively seal the channel from the first volume, wherein in the sealing configuration the resilient seal fluidly seals the valve to the container so as to fluidly isolate said second opening of the channel from the first volume, and in the open configuration the resilient seal does not fluidly seal against the container to fluidly seal the valve to the container so that the second opening of the channel is in fluid communication with the first volume; and
wherein the resilient seal is moveable from the sealing configuration to the open configuration upon fluid pressure in the first volume or second volume exceeding a first pressure threshold.

In one embodiment, the resilient seal preferably comprises one or more flexible elements, wherein, preferably, said one or more flexible elements partly extends circumferentially around said valve and the remainder of the valve forms a seal with the container circumferentially around said one or more flexible elements. Alternatively preferably, said one or more flexible elements extends entirely circumferentially around said valve.

The resilient seal may comprise at least two flexible elements, wherein the at least two flexible elements may be axially aligned with one another.

In one embodiment, the channel preferably comprises at least one axial channel part and at least one additional channel part arranged substantially perpendicularly to said at least one axial channel and in fluid communication therewith.

Preferably, the permanent seal comprises at least one flange projecting outwardly from said valve about the entire perimeter of the valve. The permanent seal preferably comprises at least two flanges projecting outwardly from said valve about the entire perimeter of the valve, wherein the at least two flanges are arranged in axial alignment with one another.

Said plunger element preferably comprises a plunger stopper and a plunger rod connected to the plunger stopper for axially moving the plunger stopper in the container.

Said valve may comprise elastomeric material.

Said permanent seal may comprise a weld between the valve and the container. In one preferable embodiment, said weld is a radio frequency (RF) weld. In an alternative preferable embodiment, said weld is a heat weld.

In one embodiment, said permanent seal includes an adhesive join between the valve and the container.

In another preferable embodiment, forward axial movement of the valve relative to the container is inhibited by one or more formations projecting radially inwardly from an interior surface of the container at an axial location that is axially forwards of the permanent seal. The valved container assembly may further comprise one or more formations projecting radially inwardly from an interior surface of the container at an axial location that is axially rearwards of the permanent seal.

In accordance with a second aspect of the present invention, there is provided a nasal dispenser comprising the valved container assembly of the first aspect of the present invention.

In accordance with a third aspect of the present invention, there is provided a valved container assembly comprising:
- a container for containing a fluid, the container extending in an axial direction and having an open front end;
- a valve disposed in the container; and
- a plunger element disposed axially rearward of the valve, the plunger element being axially moveable in the container and wherein a first volume is provided in the container between the plunger element and the valve, wherein the plunger element is configured to increase a pressure of the fluid in the first volume upon axial movement of the plunger element relative to the valve;

wherein the valve comprises:
- a seal fluidly sealing the valve to an interior of the container along an entire perimeter of the valve; and a channel bypassing the seal, the channel having a first opening in fluid communication with an atmosphere outside of the valve container assembly and a second opening selectively sealed from the first volume by a resilient seal;

wherein the resilient seal is moveable between a sealing configuration and an open configuration to selectively seal the channel from the first volume, wherein in the sealing configuration the resilient seal fluidly seals against the container to fluidly seal the valve to the container so as to fluidly isolate the channel from the first volume, and in the open configuration the resilient seal does not fluidly seal against the container to fluidly seal the valve to the container so that the second opening of the channel is in fluid communication with the first volume; and wherein the resilient seal is moveable from the sealing configuration to the open configuration upon the pressure of the fluid in the first volume exceeding a first pressure threshold.

In one embodiment, the resilient seal preferably comprises one or more flexible elements, wherein, preferably, said one or more flexible elements partly extends circumferentially around said valve and the remainder of the valve seals with the container circumferentially around said one or more flexible elements. Alternatively preferably, said one or more flexible elements extends entirely circumferentially around said valve.

The seal may comprise at least two flexible elements, wherein the at least two flexible elements may be axially aligned with one another.

In one embodiment, the channel preferably comprises at least one axial channel part and at least one additional channel part arranged substantially perpendicularly to said at least one axial channel and in fluid communication therewith.

Preferably, the seal comprises at least one flange projecting outwardly from said valve about the entire perimeter of the valve. The seal preferably comprises at least two flanges projecting outwardly from said valve about the entire perimeter of the valve, wherein the at least two flanges are arranged in axial alignment with one another.

Said plunger element preferably comprises a plunger stopper and a plunger rod connected to the plunger stopper for axially moving the plunger stopper in the container.

Said valve may comprise elastomeric material.

Said seal may comprise a weld between the valve and the container. In one preferable embodiment, said weld is a radio frequency (RF) weld. In an alternative preferable embodiment, said weld is a heat weld.

In one embodiment, said seal includes an adhesive join between the valve and the container.

In another preferable embodiment, forward axial movement of the valve relative to the container is inhibited by one or more formations projecting radially inwardly from an interior surface of the container at an axial location that is axially forwards of the seal. The valved container assembly may further comprise one or more formations projecting radially inwardly from an interior surface of the container at an axial location that is axially rearwards of the seal.

In accordance with a fourth aspect of the present invention, there is provided a nasal dispenser comprising the valved container assembly of the third aspect of the present invention.

In accordance with a fifth aspect of the present invention, there is provided a method of using a valved container assembly comprising the steps of:

i) providing the valved container assembly according to the first or third aspect of the present invention containing a fluid in the first volume; and ii) moving the plunger element axially forwardly relative to the valve to pressurise the fluid so that the resilient seal moves to the open configuration and permits the expulsion of the fluid through the valve via the channel.

BRIEF DESCRIPTION OF THE DRAWINGS

Embodiments of the invention are further described hereinafter with reference to the accompanying drawings, in which:

FIG. 1A shows the valved container assembly prior to actuation, FIG. 1B shows the valved container assembly during delivery, and FIG. 1C shows the valved container assembly after delivery;

DETAILED DESCRIPTION

Figure 1A:
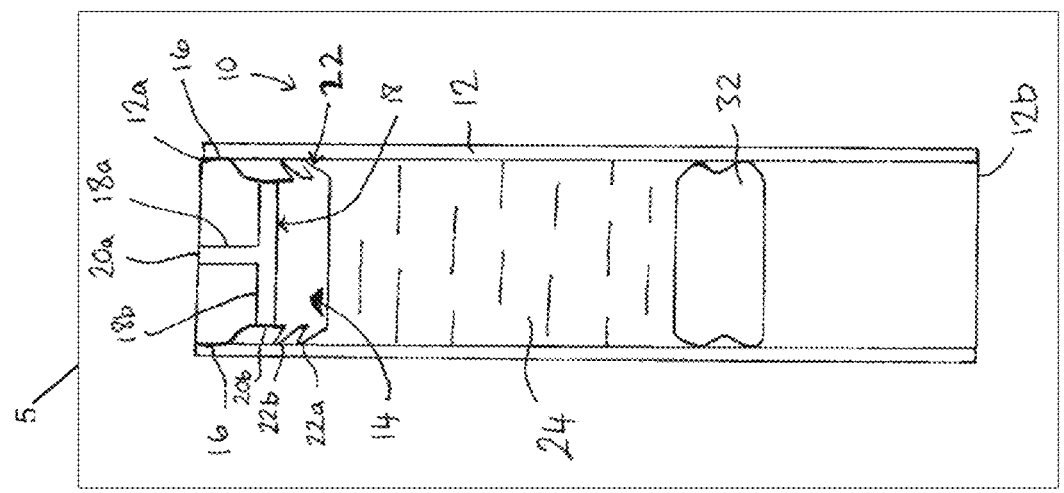
FIGS. 1A to 1C are cross sectional views of a valved container assembly in accordance with an embodiment of the present invention, in various stages of its operation, where
Figure 1B:
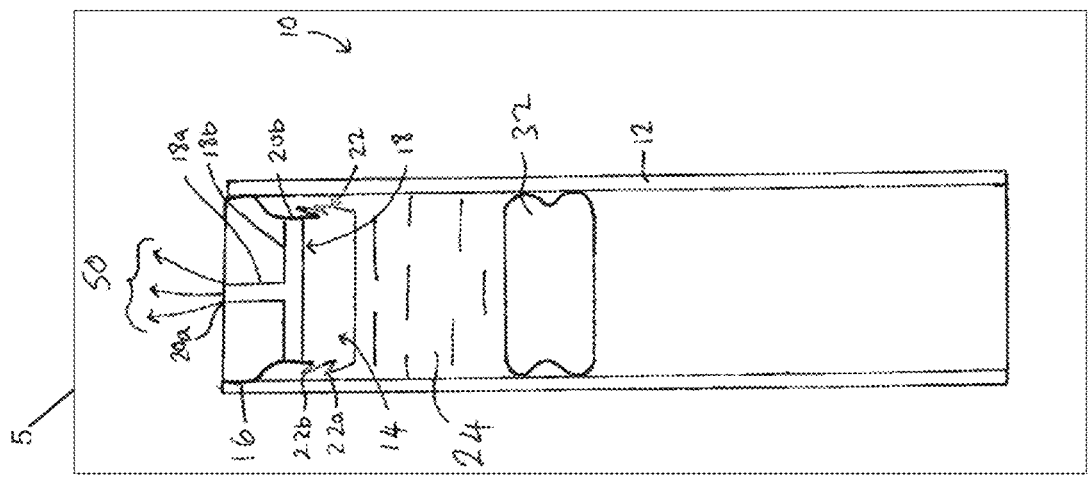
Figure 1C:
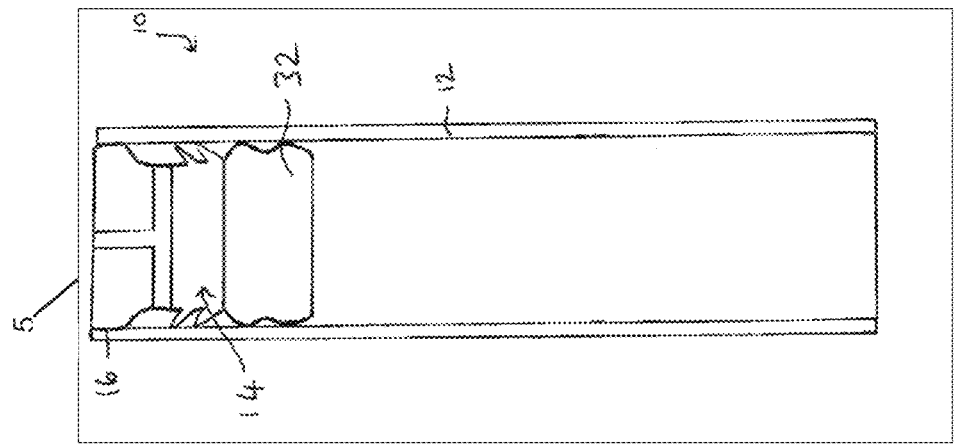

FIGS. 1A to 1C show the various stages of operation of a valved container assembly 10 in accordance with one embodiment of the present invention. The valved container assembly 10, which is illustratively shown as a nasal dispenser 5, comprises a container 12 that is preferably cylindrical, a valve 14 disposed in the container 12 and a plunger element 32 disposed in the container 12. The container 12 extends along a longitudinal axis between an open front end 12a and an open rear end 12b. Hereinafter, references to "forward" or "front" or the like are in reference to the open front end 12a of the container 12, likewise references to "rearward" or "rear" or the like are in reference to the open rear end 12b of the container 12, and references to "axial" or the like are considered to denote directions parallel to the longitudinal axis of the container.

Figure 3:
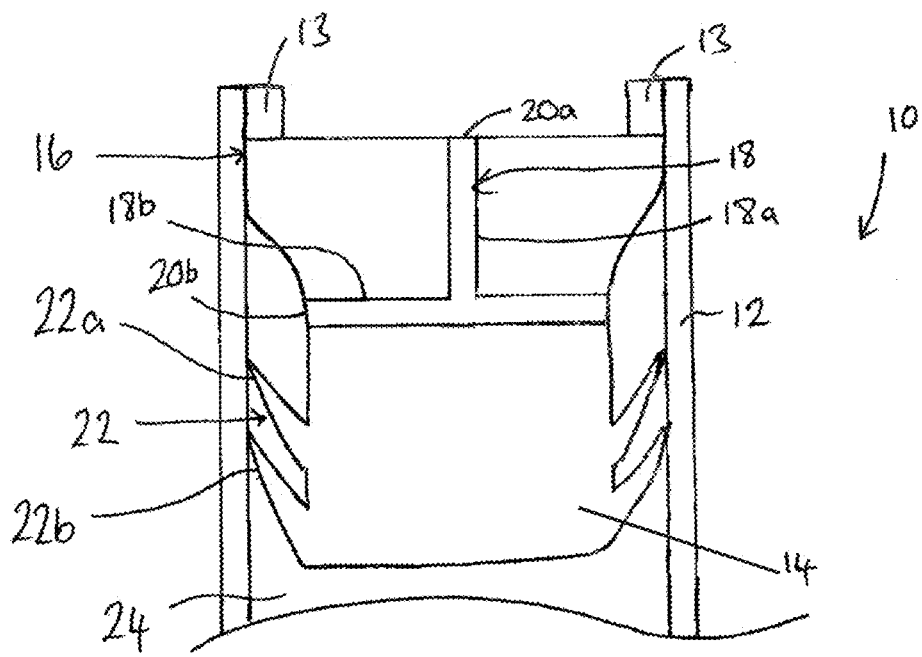
FIG. 3 shows a partial cross sectional view of a valved container assembly in accordance with an alternative embodiment of the present invention.

The valve 14 is disposed in the container 12 at or near the open front end 12a and comprises a permanent seal 16 that forms a fluid tight seal with the interior of the container 12 around the entire periphery of the valve 14. The permanent seal 16 may be formed by a permanent fixation between the valve 14 and the container such as a radio frequency (RF) weld or heat weld, or by an alternative fixing means such as a suitable adhesive. In an alternative embodiment, the valve 14 may be elastomeric and the permanent seal 16 may be formed by the elastomeric nature of the valve 14, with the permanent seal 16 bearing against the container 12. In this alternative embodiment, the valve 14 must be retained axially within the container 12 so that it does not move axially forwardly, and certainly does not exit the container 12 through the open front end 12a. For example, as shown in FIG. 3, the valve 14 may be prevented from moving axially forwardly relative to the container 12 so that the permanent seal 16 no longer seals between the valve 14 and the container 12. In the embodiment shown in FIG. 3, ribs 13 projecting radially inwardly from the interior surface of the container inhibit forward axial movement of the valve 14 relative to the container 12. One or more ribs 13 or alternative formations may be employed to prevent forward axial movement of the valve 14 relative to the container 12. The ribs 13 or alternative formations may extend partly or entirely around the inner circumference of the container 12. In a further embodiment, further ribs or alternative formations may be disposed axially rearward of the permanent seal 16 so as to inhibit axially rearward movement of the valve 14 relative to the container 12.

Axially rearward of the permanent seal 16, the valve 14 has a resilient seal 22 that is formed of a pair of axially aligned flexible elements 22a, 22b that extend radially from the valve 14 and extend around the entire periphery of the valve 14. As is described in more detail below, the resilient seal 22 is moveable between a sealing configuration (as shown in FIG. 1A) and an open configuration (as shown in FIG. 1B), wherein in the sealing configuration, the resilient seal 22 fluidly seals the valve 14 to the container 12, and in the open configuration, the resilient seal 22 does not fluidly seal the valve 14 to the container 12.

Between the valve 14 and the plunger element 32 is defined a first volume 24 that can contain a fluid such as a fluidic medicament.

A channel 18 passes through the valve 14 and has a first opening 20a which vents to the atmosphere outside of the container 12 and two second openings 20b that are each selectively sealed from the first volume 24 by the resilient seal 22. In the embodiment shown in FIGS. 1A to 1C, the channel 18 has a first axial channel part 18a and a second channel part 18b arranged substantially perpendicularly to the first axial channel part 18a. The first opening 20a is associated with the first axial channel part 18a and the two second openings 20b are associated with the second channel part 18b. In the specific embodiment depicted in FIGS. 1A to 1C, the channel 18 is T-shaped in cross-section.

When the resilient seal 22 is in the sealing configuration, the first volume 24 is fluidly sealed within the container by the valve 14. Conversely, when the resilient seal 22 is in the open configuration the first volume 24 is in fluid communication with the atmosphere via the channel 18. Thus, since the resilient seal 22 is moveable between the sealing configuration and the open configuration, so too is the valve 14 as a whole, since it selectively fluidly isolates and fluidly connects the first volume 24 to the atmosphere via the channel 18 depending on the configuration of the resilient seal 22.

The resilient seal 22 is moved from the sealing configuration to the open configuration when a force incident on the resilient seal 22 exceeds a predetermined threshold. Such a force will arise when the fluid pressure of a fluid acting on the resilient seal 22 exceeds a predetermined threshold. For example, if the first volume was filled with a fluid (such as a fluidic medicament), then the resilient seal 22 would move from the sealing configuration to the open configuration when the pressure of the fluid exceeded the predetermined threshold. When the pressure exceeds the predetermined threshold, the flexible elements 22a, 22b of the resilient seal 22 flex or deflect so as to move away from the container 12 and open a fluid pathway allowing fluid to bypass the resilient seal 22. Alternative components may form the resilient seal 22 in place of the flexible elements 22a, 22b that deform, deflect, flex or otherwise move to open a fluid pathway between the valve 14 and the container 12 upon application of a predetermined force. In the embodiment shown in FIG. 1B, the flexible elements 22a, 22b are shown to be flexed or deflected in a forward direction, such as one might expect to result from the pressure of a fluid in the first volume exceeding the predetermined pressure threshold.

In both sealing and open configurations, the permanent seal 16 remains in place and maintains a seal between the valve 14 and the container 12 axially forwards of the resilient seal 22. Thus, a fluid connection is only formed between the first volume 24 and the atmosphere when the resilient seal 22 is in the open configuration. Even when the resilient seal 22 is in the open configuration, fluid must flow along several axes in order to bypass the permanent seal 16 through the channel 18. This arrangement therefore provides a labyrinth pathway between the first volume 24 and the atmosphere, as opposed to a straight channel. A benefit of the labyrinth arrangement is that the likelihood of fluid flow from the first volume to the atmosphere is substantially reduced in the event that the resilient seal 22 is inadvertently moved to the open configuration for a short period of time. One advantage of having the resilient seal 22 acting between the valve 14 and the container 12 is that this provides a low friction arrangement (particularly when the internal surface of the container 12 is siliconised, which it often is) making the resilient seal 22 more reliable at opening when desired, since friction will have less influence of the predetermined pressure threshold.

FIG. 1A shows the valved container assembly 10 prior to actuation. The first volume 24 contains a fluid and the resilient seal 22 is in its sealing configuration. To actuate the device to dispense the fluid from the container 12, the user applies an axially forward force to the plunger element 32 to increase the pressure of the fluid above the predetermined threshold. Because the valve 14 is axially fixed in the container 12, it remains axially stationary and is acted upon by the force applied to the plunger element 32 due to the incompressible nature of fluid. The resilient seal 22 is therefore acted upon by the fluid, which is above the predetermined threshold, and the resilient seal moves from the sealing configuration to the open configuration.

When in the open configuration, further axially forward movement of the plunger element 32 relative to the fixed valve 14 causes the fluid to flow from the first volume out through the first opening 20a of the channel 18 as depicted by arrows 50 in FIG. 1B.

Continued axially forward movement of the plunger element 32 relative to the fixed valve 14 causes all of the fluid in the first volume 24 to be expelled through the channel 18, and the first volume is reduced to substantially zero, as shown in FIG. 1C. At this point, the dispensing operation is complete.

The plunger element 32 may be accessed through the open rear end 12b of the container 12 and may additionally include a plunger rod or the like to facilitate its axial movement within the container 12.

Figure 2A:
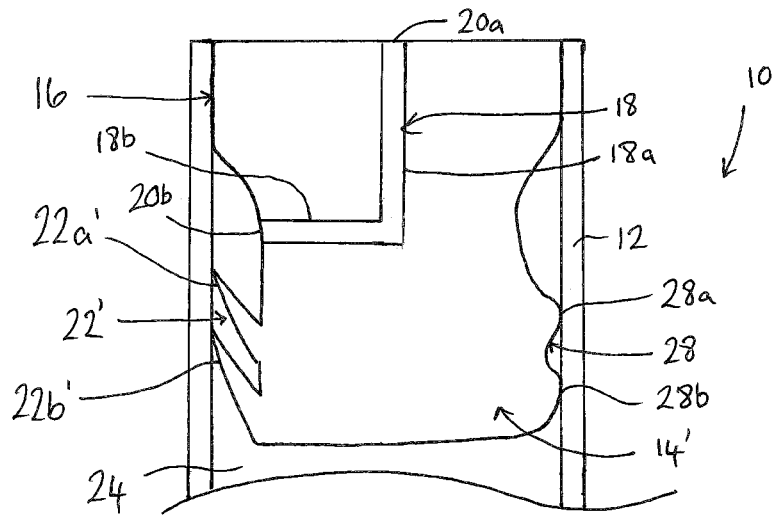
FIG. 2A shows a partial cross sectional view of a valved container assembly which has an alternative valve in accordance with one embodiment of the present invention, where the valve is in a sealing configuration.
Figure 2B:
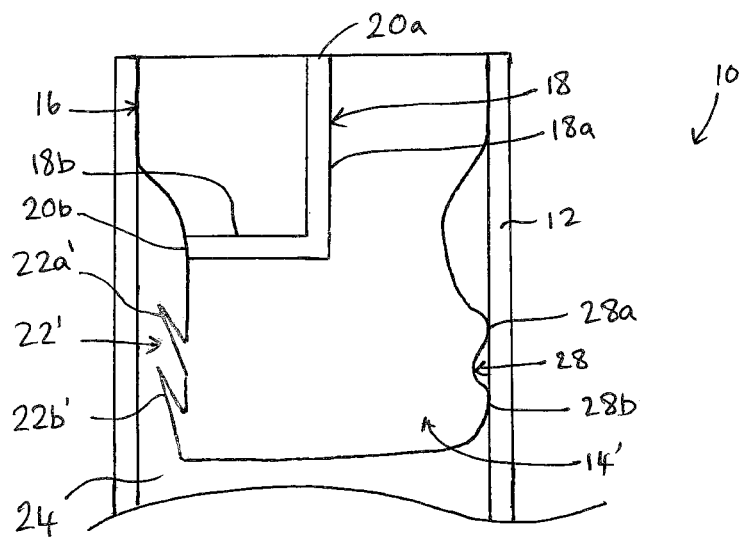
FIG. 2B shows the valved container assembly of FIG. 2A where the valve is in an open configuration.

An alternative embodiment of the invention is shown in FIGS. 2A and 2B in which the valved container assembly 10 comprises an alternative valve 14'. Apart from the alternative valve 14', the valved container assembly 10 is otherwise identical to that described above in relation to FIGS. 1A to 1C. Indeed, the ribs or alternative formations described above in relation to FIG. 3 may also be employed on the embodiment described in relation to FIGS. 2A and 2B. The alternative valve 14' has a permanent seal 16 identical to that described above in relation to FIGS. 1A to 1C, and comprises a resilient seal 22. The resilient seal 22 depicted in FIGS. 2A and 2B is formed of a pair of flexible elements 22a', 22b' each extending radially from the valve 14' and arranged in axial alignment with one another. However, different to the resilient seal 22 of FIGS. 1A to 1C, the resilient seal 22' of FIGS. 2A and 2B does not extend entirely circumferentially around the valve 14' but is otherwise identical to resilient seal 22. Instead, the resilient seal 22' extends partly around the circumference of the valve 14' and a second permanent seal 28 formed of a pair of flanges 28a, 28b extending radially from the valve 14' extend around the remainder of the circumference of the valve 14' The second permanent seal 28 maintains a permanent seal between the valve 14' and the container 12 across the extent of the circumference that it extends.

The valve 14' has a channel 18 that bypasses the permanent seal 16 and is formed of a first axial channel part 18a and a second channel part 18b arranged substantially perpendicularly to the first axial channel part 18a. A first opening 20a is associated with the first axial channel part 18a and a single second opening 20b is associated with the second channel part 18b. The channel 18 of FIGS. 2A and 2B is L-shaped in cross section, in contrast to the channel 18 of FIGS. 1A to 1C, which is T-shaped in cross section. However, either channel arrangement may be used in either embodiment. Alternatively, other channel arrangements may be employed that bypass the permanent seal 16 from an outer radial position via an inner radial position that is radially inwards of the permanent seal 16.

In preferable embodiments, the valve 14, 14' is made from a deformable elastomeric material that is able to achieve a fluid tight seal with the container 12.

The resilient seal 22' and the second permanent seal 28 are arranged relative to one another such that when the resilient seal 22' is in the sealing configuration (as shown in FIG. 2A) the combination of the resilient seal 22' and the second permanent seal 28 fluidly isolate the second opening 20b of the channel 18 from the first volume 24, and hence fluidly isolate the first volume 24 from the atmosphere. In the open configuration (as shown in FIG. 2B), the resilient seal 22' permits a fluid pathway that fluidly connects the first volume 24 to an annulus circumferentially surrounding the valve 14' between the axial positions of the permanent seal 16 and the second permanent seal 28.

In an alternative embodiment, axial ribs or similar formations (not shown) may be arranged on the valve 14' on either side of the second opening 20b in each circumferential direction so as to form an axial channel that forms a circumferential boundary around the second opening 20b and seals with the container 12. In this embodiment, the axial channel would be bound at a forward end by the permanent seal 16 and the axial channel would be bound at a rear end by resilient seal 22'. Since the second opening 20b is disposed within the bound axial channel, the second permanent seal 28 would not be necessary, however it is preferable that it still be present to minimise the risk of inadvertent fluid flow from the first volume 24 to the atmosphere.

The valved container assembly 10 of the present invention may be formed by fixing the valve 14 in place in the container 12 by one of the methods described above. A fluid may then be introduced into the container 12 and the plunger element 32 may then be inserted to contain the fluid in the first volume 24 between the plunger element 32 and the valve 14.

The first opening 20a of the valve may be provided with a spray head, nozzle or other suitable applicator to distribute the fluid exiting therefrom.

Further valves 14, 14' may be included in the container axially rearward of the first valve 14, 14' to permit the separation and subsequent expulsion (which may be sequential) of two or more substances from the container.

In the valved container assembly 10 of the present invention, the substance contained in the first volume 24 is only in contact with a limited number of materials, for example the valve 14 and the container 12. With limited contact between the materials of the valved container assembly 10 and the substance contained in the first volume 24, it is easier to determine extractables and leachables.

The container assembly 10 of the present invention affords easy and cost effective manufacture and does not necessarily require any specialist filling or assembly apparatus.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A valved container assembly comprising:
   a container for containing a fluid, the container extending in an axial direction and having an open front end;
   a valve disposed in the container; and
   a plunger element disposed axially rearward of the valve, the plunger element being axially moveable in the container and wherein a first volume is provided in the container between the plunger element and the valve, wherein the plunger element is configured to increase a pressure of the fluid in the first volume upon axial movement of the plunger element relative to the valve;
   wherein the valve comprises:
   a seal fluidly sealing the valve to an interior of the container along an entire perimeter of the valve; and
   a channel bypassing the seal, the channel having a first opening in fluid communication with an atmosphere outside of the valved container assembly and a second opening selectively sealed from the first volume by a resilient seal;
   wherein the resilient seal is moveable between a sealing configuration and an open configuration to selectively seal the channel from the first volume, wherein in the sealing configuration the resilient seal fluidly seals against the container to fluidly seal the valve to the container so as to fluidly isolate the channel from the first volume, and in the open configuration the resilient seal does not fluidly seal against the container to fluidly seal the valve to the container so that the second opening of the channel is in fluid communication with the first volume; and wherein the resilient seal is moveable from the sealing configuration to the open configuration upon the pressure of the fluid in the first volume exceeding a first pressure threshold.

2. The valved container assembly according to claim 1, wherein the resilient seal comprises one or more flexible elements.

3. The valved container assembly according to claim 2, wherein said one or more flexible elements partly extends circumferentially around said valve and the remainder of the valve forms a further seal with the container circumferentially around said one or more flexible elements.

4. The valved container assembly according to claim 2, wherein said one or more flexible elements extends entirely circumferentially around said valve.

5. The valved container assembly according to claim 2, wherein the one or more flexible elements of the resilient seal comprises at least two flexible elements.

6. The valved container assembly according to claim 5, wherein the at least two flexible elements are axially aligned with one another.

7. The valved container assembly according to claim 1, wherein the channel comprises at least one axial channel part and at least one additional channel part arranged substantially perpendicularly to said at least one axial channel part and in fluid communication therewith.

8. The valved container assembly according to claim 1, wherein the seal comprises at least one flange projecting outwardly from said valve along the entire perimeter of the valve.

9. The valved container assembly according to claim 8, wherein the seal comprises at least two flanges projecting outwardly from said valve along the entire perimeter of the valve, wherein the at least two flanges are arranged in axial alignment with one another.

10. The valved container assembly according to claim 1, wherein said plunger element comprises a plunger stopper and a plunger rod connected to the plunger stopper for axially moving the plunger stopper in the container.

11. The valved container assembly according to claim 1, wherein said valve comprises elastomeric material.

12. The valved container assembly according to claim 1, wherein said seal comprises a weld between the valve and the container.

13. The valved container assembly according to claim 12, wherein said weld is a radio frequency (RF) weld.

14. The valved container assembly according to claim 12, wherein said weld is a heat weld.

15. The valved container assembly according to claim 1, wherein said seal includes an adhesive join between the valve and the container.

16. The valved container assembly according to claim 1, wherein forward axial movement of the valve relative to the container is inhibited by one or more formations projecting radially inwardly from an interior surface of the container at an axial location that is axially forwards of the seal.

17. The valved container assembly according to claim 16, further comprising one or more of the one or more formations projecting radially inwardly from the interior surface of the container at an axial location that is axially rearwards of the seal.

18. A nasal dispenser comprising the valved container assembly of claim 1.

19. A method of using a valved container assembly comprising the steps of:
i) providing the valved container assembly including a container for containing a fluid, the container extending in an axial direction and having an open front end;
a valve disposed in the container; and
a plunger element disposed axially rearward of the valve, the plunger element being axially moveable in the container and wherein a first volume is provided in the container between the plunger element and the valve, wherein the plunger element is configured to increase a pressure of the fluid in the first volume upon axial movement of the plunger element relative to the valve;
wherein the valve comprises:
a seal fluidly sealing the valve to an interior of the container along an entire perimeter of the valve; and
a channel bypassing the seal, the channel having a first opening in fluid communication with an atmosphere outside of the valved container assembly and a second opening selectively sealed from the first volume by a resilient seal;
wherein the resilient seal is moveable between a sealing configuration and an open configuration to selectively seal the channel from the first volume, wherein in the sealing configuration the resilient seal fluidly seals against the container to fluidly seal the valve to the container so as to fluidly isolate the channel from the first volume, and in the open configuration the resilient seal does not fluidly seal against the container to fluidly seal the valve to the container so that the second opening of the channel is in fluid communication with the first volume;
wherein the resilient seal is moveable from the sealing configuration to the open configuration upon fluid pressure in the first volume exceeding a first pressure threshold and containing the fluid in the first volume; and
ii) moving the plunger element axially forwardly relative to the valve to pressurize the fluid so that the resilient seal moves to the open configuration and permits the expulsion of the fluid through the valve via the channel.

* * * * *